United States Patent
Stolz et al.

(10) Patent No.: US 6,477,427 B1
(45) Date of Patent: Nov. 5, 2002

(54) IMPLANTABLE STIMULATION LEAD AND METHOD OF MANUFACTURE

(75) Inventors: Brian T. Stolz, Bloomington, MN (US); Michael D. Baudino, Coon Rapids, MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/539,833

(22) Filed: Mar. 31, 2000

(51) Int. Cl.$^7$ .................................................. A61N 1/05
(52) U.S. Cl. ...................................... 607/116; 607/117
(58) Field of Search .................. 600/372–375, 600/393, 377–378, 380–381; 607/115–117, 119, 122, 123

(56) References Cited

U.S. PATENT DOCUMENTS

| | | | |
|---|---|---|---|
| 4,437,474 A | * 3/1984 | Peers-Trevarton | ........... 29/605 |
| 4,458,695 A | * 7/1984 | Peers-Trevarton | .......... 607/123 |
| 4,484,586 A | 11/1984 | McMickle et al. | |
| 4,630,611 A | * 12/1986 | King | ........................... 600/377 |
| 5,016,646 A | 5/1991 | Gotthardt et al. | |
| 5,324,327 A | 6/1994 | Cohen | |
| 5,330,521 A | 7/1994 | Cohen | |
| 5,374,285 A | * 12/1994 | Vaiani et al. | ................. 607/117 |
| 5,458,629 A | * 10/1995 | Buadino et al. | ............. 607/116 |
| 5,483,022 A | 1/1996 | Mar | ......................... 174/128.1 |
| 5,571,157 A | 11/1996 | McConnell | |
| 5,760,341 A | 6/1998 | Laske et al. | .............. 174/126.2 |
| 5,800,496 A | 9/1998 | Swoyer et al. | |
| 5,855,552 A | * 1/1999 | Houser et al. | ............... 607/122 |
| 5,968,087 A | 10/1999 | Hess et al. | |
| 6,185,463 B1 | * 2/2001 | Baudino | ...................... 607/119 |

* cited by examiner

Primary Examiner—Kennedy Schaetzle
Assistant Examiner—Kristen Droesch
(74) Attorney, Agent, or Firm—Banner & Witcoff, Ltd.

(57) ABSTRACT

An implantable lead and an improved method of manufacture is disclosed that is highly automated and simplified over prior art techniques. An implantable lead is disclosed having a flexible tubing member, a central coil member having a first portion having differing pitches, and a least one contact sleeve having a through radial hole for receipt of the wire member. A method for manufacture of the lead is disclosed by providing a coil member having a fixed pitch portion and a variable pitch portion, extending at least one filar member radially from the coil member, placing a lead body over the coil member, providing a contact sleeve over a portion of the lead body, the contact sleeve having a slot for receipt of the filar member, and welding the filar member to the contact sleeve.

22 Claims, 7 Drawing Sheets

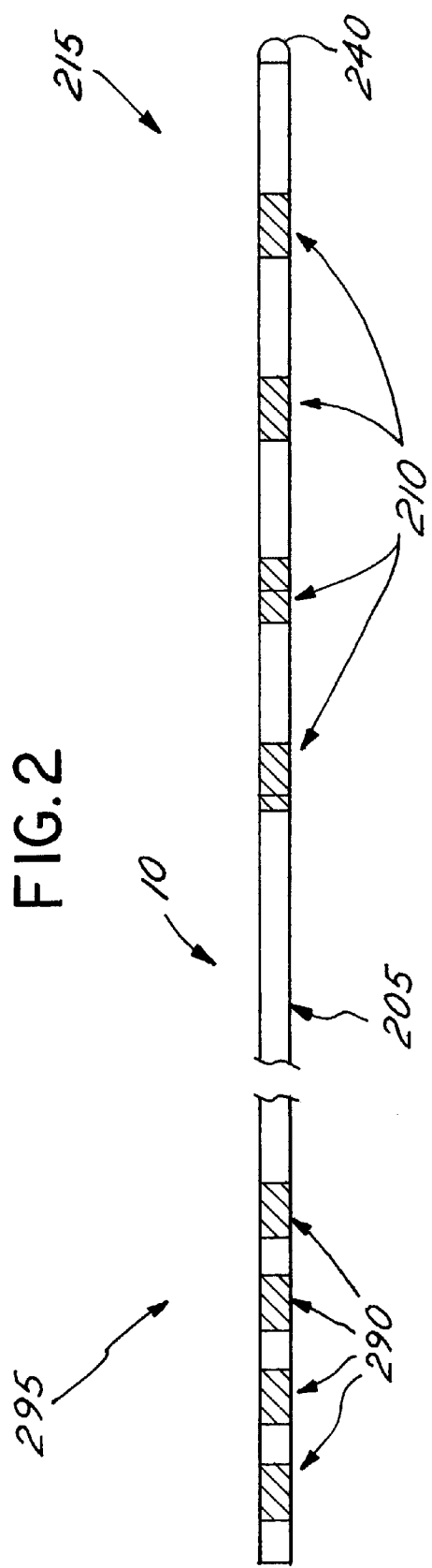

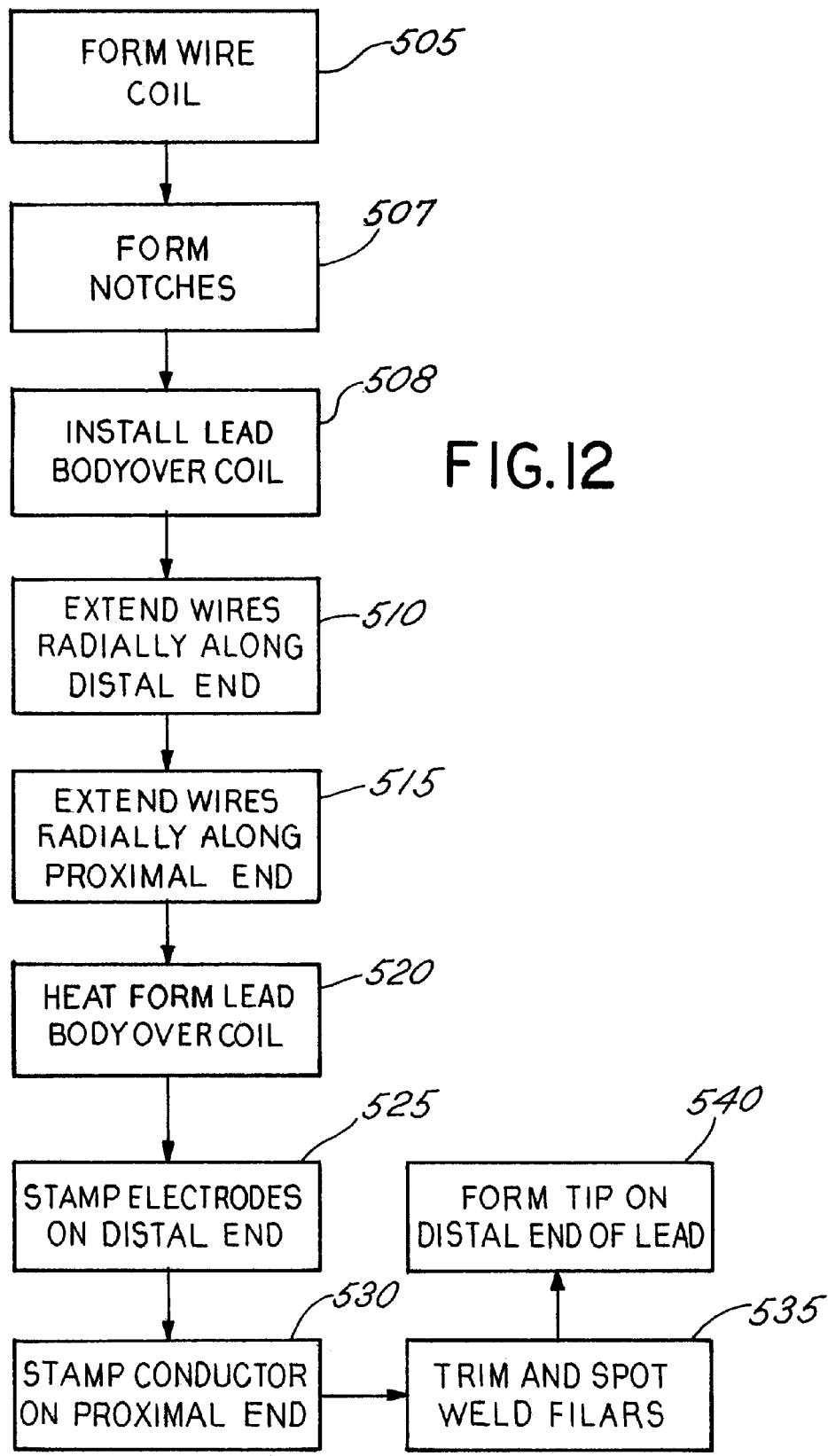

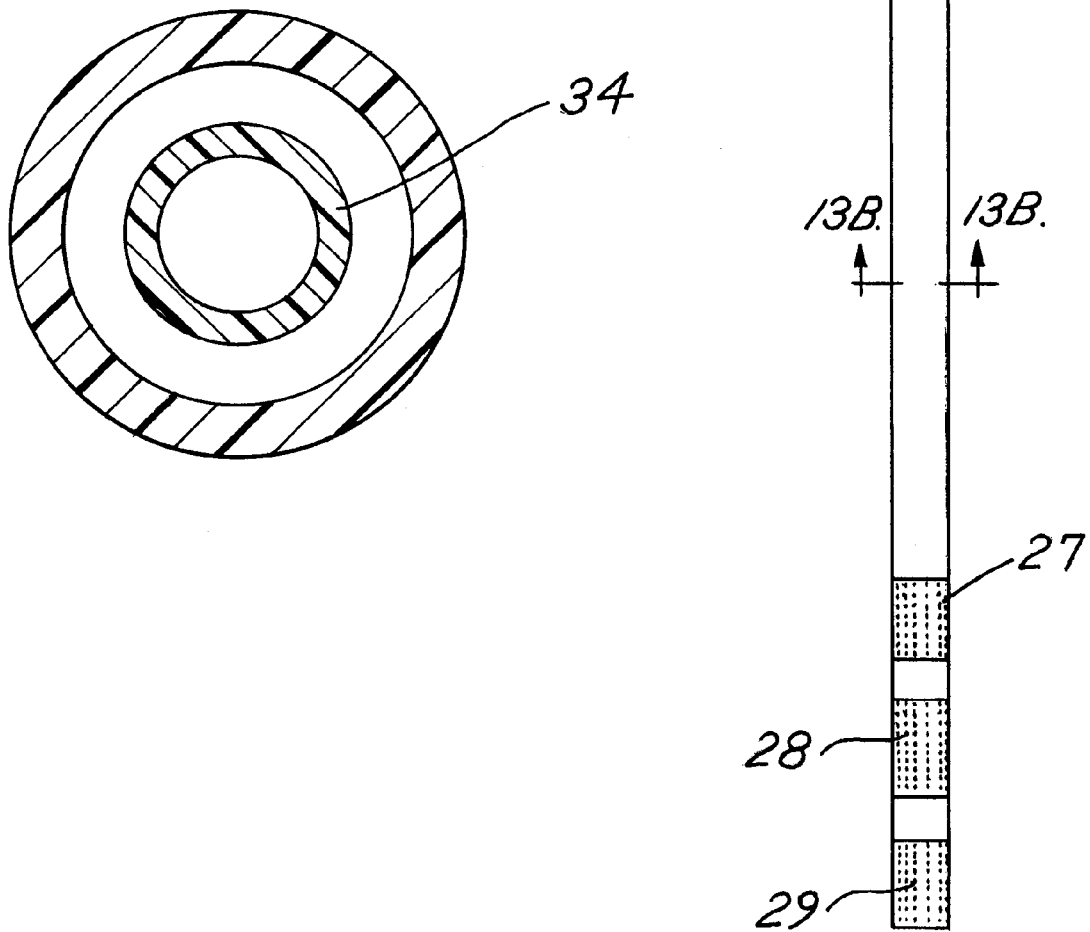

IMPLANTABLE STIMULATION LEAD AND METHOD OF MANUFACTURE

BACKGROUND OF THE INVENTION

1. Field of the Invention

This invention relates to implantable devices and more particularly relates to the design and manufacture of implantable leads.

2. Description of the Related Art

An increasingly popular technique for therapeutically treating neurological disorders and chronic pain is providing electrical stimulation to neural tissue within the brain, the spinal cord, and/or a peripheral nerve. Thus, for example, physicians may surgically implant leads having electrode contacts near the spinal column of the human body and deliver electrical energy, using a signal generator, to these contacts to stimulate targeted neural tissue and elicit the desired therapeutic relief.

Implantable leads now also provide electrical stimulation via more than one electrode. This significantly increases the functionality of the implantable lead. For example, a multiple electrode lead allows the physician to adjust the treatment therapy to target different neural tissue, or to direct the stimulation more precisely to the neural tissue of interest. This is particularly useful where the implanted lead migrates along the spinal cord after it has been implanted. By subsequently adjusting the electrical stimulation delivered by the multi-electrode lead, the need for a second surgery is avoided.

A commonly-used implantable lead is a Pisces-style lead. As depicted in FIGS. 1A and 1B, this lead is a long and narrow tube, typically polyurethane, having an outside diameter of 0.050" and an inside diameter of 0.030". Along the distal end 120 of the lead are one or more electrodes 105 that wrap around the circumference of the lead body and have a certain width. These electrodes 105 are coupled to respective wires 110 that run from within a lumen 117 of the lead tubing to corresponding connectors 115 along the proximal end 125 of the lead. Most implantable leads utilized today are based on a coiled-spring design. In such leads, the wires that are used to connect the lead to the electrodes are wrapped around a mandrel with enough tension to cause the wires to exceed their yield point and thus to hold a coiled shape. The coiled wires are insulated from each other and typically have a fixed pitch, namely a fixed number of revolutions per inch. Each coiled wire is coupled to a corresponding electrode along the lead body. This is achieved by having the distal end of the wire (the filar) exit tangentially from the coil along the distal end of the lead and then be connected to an electrode located at that portion of the lead.

The coiled-spring design of the implantable leads, however, is limiting in its difficulty of assembly with the electrodes. In particular, the coiled-spring wires are unwound along the distal end of the lead and extended tangentially from the coil at along the desired portion of the lead where the corresponding electrode for each wire is to be placed. The tangentially extending wires are typically referred to as filars. This unwinding process, however, is inaccurate resulting in the filars extending unevenly from the coil. This results in non-coplanar weld placement of the electrode contacts over the filars.

After placement of the electrodes, the filars are positioned and trimmed while maintaining contact with the corresponding electrodes. A filar for the wire corresponding to an electrode is placed within a slot of the electrode and put in contact with that electrode and welded. The resulting weld, however, often protrudes from the surface of the lead, potentially causing interference during implant.

Further inefficiencies result in the overall manufacture of the Pisces-style lead. Known procedures for manufacturing implantable leads require considerable steps and operator involvement. Multiple cure processes must be performed requiring as much as 2–3 days of cure time. The greater the number of leads, the greater time and cost required in manufacturing the lead. Further, manufacture of these leads requires skilled technicians to perform some of these manufacturing steps.

It is therefore desirable to provide a design for and a method of manufacture of an implantable lead that can overcome these and other disadvantages.

SUMMARY OF THE INVENTION

A preferred form of the invention is an implantable lead and a method of manufacture of the lead. The implantable lead has flexible tubing impressions, contact sleeves positioned over the impressions and having openings, and a wire coil member running along a central lumen portion of the lead. The wire coil has radially extending filars that extend in a substantially perpendicular axis relative to the surface of the wire coil. Further, the wire coil has fixed and variable pitch portions to provide accurate positioning of the radially extending filars.

The method of manufacture includes the steps of forming a coil having at least one wire member having fixed and variable pitches, each wire member having a filar member, extending the filar member of at least one of the wire members radially from the coil member at a predetermined portion along the variable pitch portion of the coil member, heat forming a flexible lead body over the coil member, providing a contact sleeve over a portion of the lead body, the contact sleeve having a opening for receipt of the filar member, and welding the filar member to the contact sleeve.

The design and process of the implantable lead of the present invention provides a number of advantages over leads of the prior art. By way of examples, the present invention provides a wire coil design that provides improved accuracy in distances between the filars and improved assembly with the electrodes. In addition, the present invention reduces the direct build time of the lead, reduces the required level of operator training to manufacture the lead, and requires less manufacturing floor space. The applicant estimates that each of these variables may be reduced by as much as 50% over prior art techniques.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 2 is a front view of an implantable lead in accordance with a preferred embodiment of the present invention;

FIG. 12 is flow chart illustrating a manufacturing process for an implantable lead in accordance with a preferred embodiment of the present invention; and FIGS. 13A and 13B are front and cross-sectional views, respectively, of an implantable lead having a concentric catheter in accordance with another preferred embodiment of the invention.

DESCRIPTION OF THE PREFERRED EMBODIMENTS

Figure 1A:
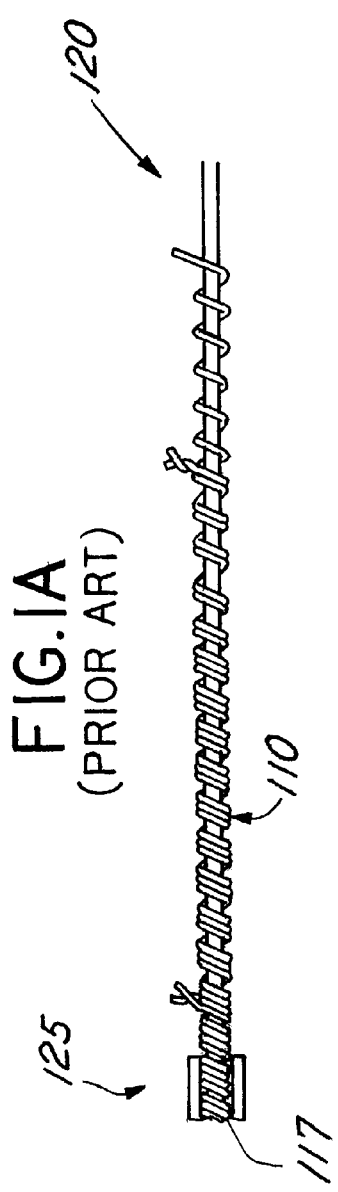
FIGS. 1A and 1B front views of an implantable lead of the prior art.
Figure 1B:
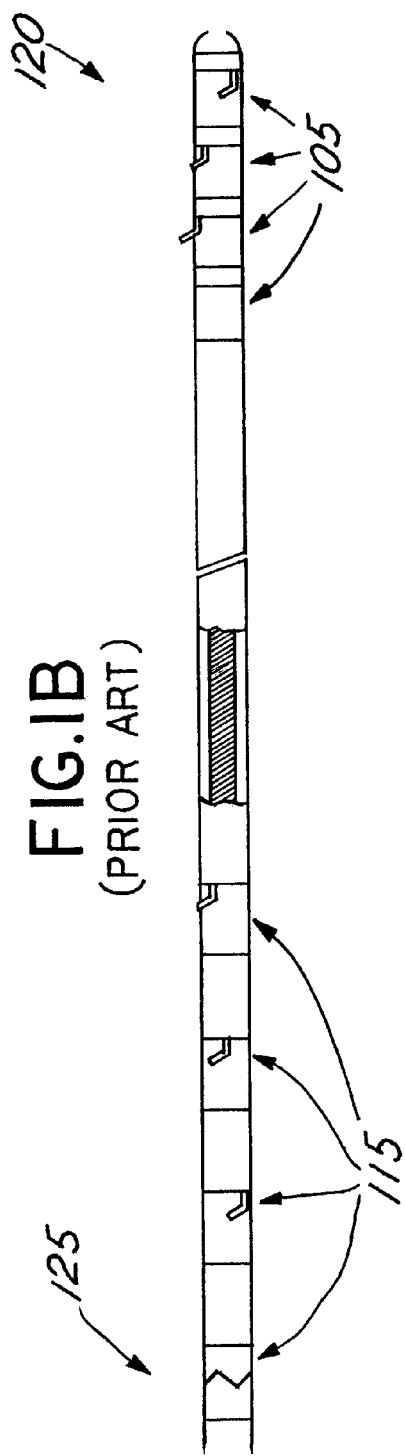

Referring to FIG. 2, a preferred form of the invention basically includes an implantable lead 10 having an outer tubing 205, a helical coil (not shown) within the tubing 205, and a plurality of electrodes 210 along the distal end 215 of the lead and a plurality of conductors 290 along the proximal end 295. Outer tubing 205 is preferably a polyurethane tubing having a 0.050" outside diameter and a 0.030" inside diameter. Other tubing materials such as silicon rubber or thermoform are also suitable. FIGS. 8–11 depict the outer tubing 205 in accordance with a preferred embodiment of the present invention. Outer tubing 205 has one or more notches 225 on the distal end, one for each electrode to be placed along the lead 10. Similarly, outer tubing 205 has one or more notches 220 on the proximal end 295, one for each connector 290 to be placed along the lead 10. Notches 220 are of variable length typically in the range from 0.06 inch to 0.24 inch, for example 0.09 inch, and have an outside diameter of approximately 0.040 inch. Similar notches 225 are positioned along the proximal end for coupling to a power source (not shown).

Referring back to FIG. 2, electrodes 210 are preferably formed electrodes 210 having an aperture along its body. The diameter of the aperture is closely matched to the diameter of the filar 235 (discussed below) of its associated wire to allow the filar 235 to be inserted within the aperture and to allow proper welding of the filar 235 to the electrode 210. Electrodes 210 are placed over the notches 220 and formed on to the lead 10.

Figure 3:
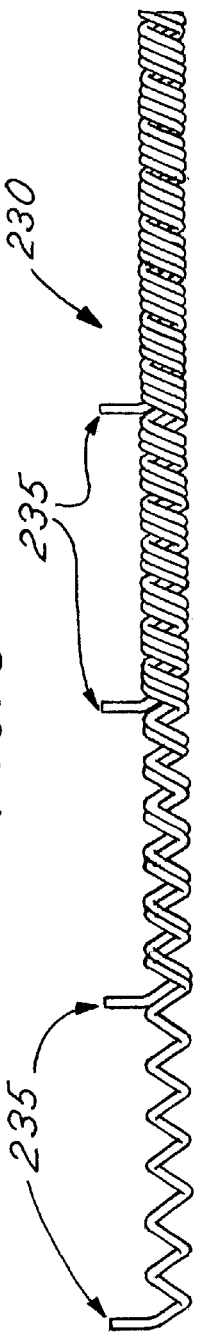
FIG. 3 is a front view of a coiled loop along the proximal end in accordance with a preferred embodiment of the present invention.
Figure 4:
FIG. 4 is a front view of the coiled loop of FIG. 3 along the main body.
Figure 5:
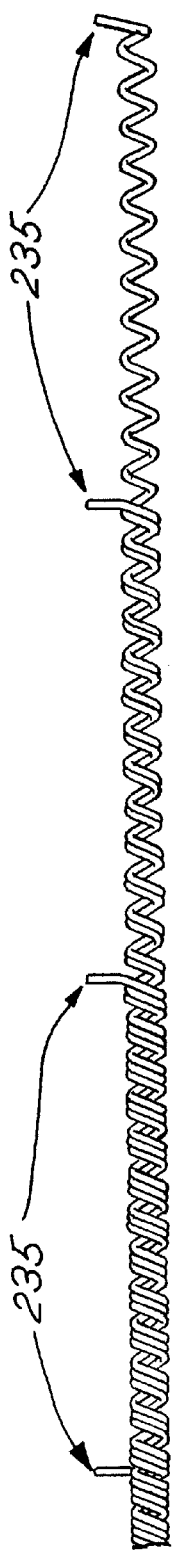
FIG. 5 is a front view of a coiled loop of FIG. 3 along the distal end.
Figure 6:
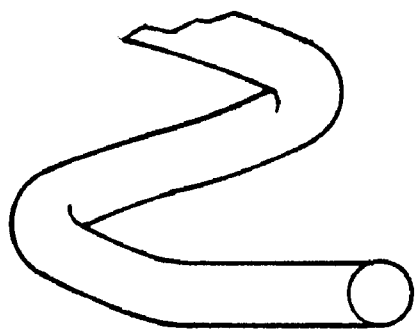
FIG. 6 is a close-up sectional view of a filar of the coiled loop of FIG. 3.
Figure 7:
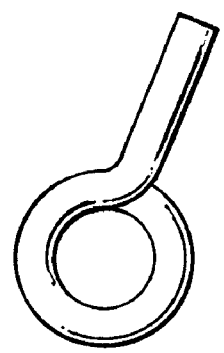
FIG. 7 is another close-up sectional view of the filar of the coiled loop of FIG. 3.
Figure 8:
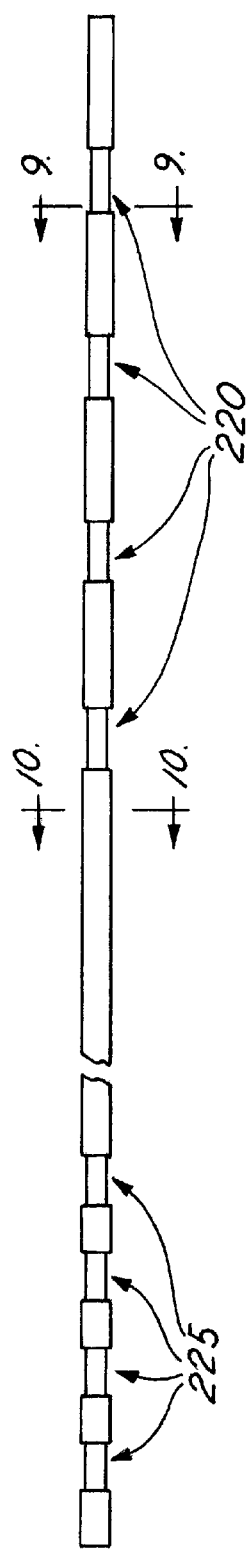
FIG. 8 is a front view of a lead body in accordance with a preferred embodiment of the present invention.
Figure 11:
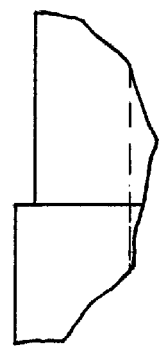
FIGS. 9–11 are sectional views of the lead body of FIG. 8.
Figure 10:
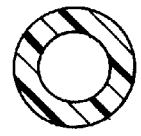
Figure 9:

FIGS. 3–7 depict the helical coil 230 fitted within the outer tubing 205. Helical coil 230 consists of a plurality of wound wires providing electrical connection to each of the electrodes 210. Each wire within the coil 230 contacts and provides electrical energy to a corresponding electrode 210 on the lead 10. As shown in FIG. 5, the distal end of each wire, or the filar 235, terminates at a designated portion of the lead 10 where the corresponding electrode 210 is located. The coils 230 are preferably wound having a portion having a fixed pitch and a portion along the electrodes 210 having a variable pitch. The variable pitch allows the filars 235 of each of the wires to be coplanar and allows the filars 235 to have the necessary spacing between each other. As preferred and as illustrated in FIGS. 6 and 7, filars 235 extend in a substantially perpendicular manner from the coil 230. Coil 230 may be formed using a programmable coil winder, which is generally known in the art. The variable pitch in the coil 230 may be formed using techniques generally understood in the art. Similarly, the proximal end of each wire terminates in filar 235 as shown in FIG. 3.

The outside diameter of coil 230 is approximately in the range of .026 inch to 0.030 inch. The pitch angle of the revolutions is in the range of 10 degrees to approaching 90 degrees. At 10 degrees, the helical coil 230 approaches a straight or linear wire whereas when it approaches 90 degrees the helical coil 230 would be considered tight or close wound.

In an alternative embodiment, shown in FIGS. 13A–B, coil 230 may be fabricated to form a hollow lumen 34 within the coil 230. A stylet may then be inserted in the lumen, and drugs may be infused through the lumen and out through microporous portions 27–29. Alternatively, a thin walled tube could be placed within coil to provide a closed conduit from proximal to distal ends of body 12. The core revolutions would "float" on the inner conduit formed by the thin walled tube. Drugs may be infused through the thin walled tube to exit the distal end of the lead or along a side wall portion. The structure of the lumen may be similar to that disclosed in U.S. Pat. Nos. 5,702,437 and 5,713,923, both of which are incorporated herein by reference in their entireties.

FIG. 12 depicts a flow chart illustrating the method of manufacture of an implantable lead in accordance with a preferred embodiment of the present invention. At step 505, a plurality of wires that are wrapped to form a coil of wires are cleaned and inspected. As discussed above, any number of techniques can be used to form the coil 230 and typically entails wrapping the wires around a mandrel. The coil 230 preferably has a constant pitch along the body of the coil 230. Approaching the distal end 215 of the coil 230, near the placement of the electrodes 210, the coil 230 has a variable pitch. As stated before, coil 230 may be formed using a programmable coil winder, which is generally known in the art.

At step 507, notches 220 and 225 are provided along the distal and proximal ends of the lead body 205 using any number of techniques, including but not limited to, grinding or laser etching. The notches 220 and 225 extend circumferentially around the lead body and serve to accommodate placement of the electrodes 210 and connectors 290 along the lead body 205. The notches 220 and 225 are preferably in the range of 0.005 inch deep.

At step 508, a polyurethane split lead body 205 is slid over the coil 230. The lead body 205 has distal and proximal slits along the distal 215 and proximal 290 ends, respectively, to receive the radially protruding filars 235 discussed below.

At step 510, each wire is extended radially away from the coil member along the distal end of the coil at the point of contact with the electrode 210 corresponding to each wire. The distal ends of the wires, known as the filars 235, extend substantially perpendicularly from the surface of the coil 230, thereby providing each of placement of the electrodes 210. In addition, the filars 235 are preferably coplanar with each other and also have a predetermined distance between the filars 235. Accordingly, pitch of the coil 230 may be calculated as a function of the distance between the filars 235. The predetermined distance between the filars 235 allows the electrode 210 to be positioned at the desired portion of the lead 10. During this process, the lead body 205 may be slid toward the proximal end 295 and away from the distal end 215 to allow unwinding of the coil member 230. After the coil 230 is unwound, the lead body 205 may slide back over the distal end 215 with the filars 235 extending through the distal slit on lead body 205.

At step 515, a similar procedure is performed at the proximal end 295 for placement of the conductors 290. Again, during this process, the lead body 205 may be slid toward the distal end 215 and away from the proximal end 295 to allow unwinding of the coil members 230. After the coil 230 is unwound, the lead body 205 may slide back over the proximal end 295 with the filars 235 extending through the proximal slit on lead body 205.

At step 520, the lead 10 is placed in a mold to heat seal the slits and to provide a final dimension for the notches 220 and 225. Advantageously, this process eliminates a number of the steps and detail required to fabricate a lead under the prior art, including, for example, eliminating the step of using a solvent and the need for a curing process.

At step 525, electrodes 210 are formed over the notches 220 of the lead body 205. The electrodes 210 have an aperture for receipt of the filars 235. Advantageously, a formed electrode 210 is easier to install than a machined electrode of the prior art and required less operator time. Similarly, at steps 530, connectors 290 are assembled and positioned in a similar manner as that described above in step. Connectors 290 also have an aperture for receipt of the filars 235.

At step 535, the filars 235 are trimmed and spot welded to their corresponding electrodes 210 and connectors 290. Alternatively, the filars 235 may be attached or connected as part of a seam weld. Advantageously, spot welds provide a convenient way of assuring that the filars 235 are in contact with the electrodes 210 and connectors 290. In particular, if the filar 235 is in contact with the electrode 210 or connector 290, the aperture of the electrode 210 or connector 290 will be filled in by the weld. If the filar 235 is not in contact with the electrode 210 or connector 290, the aperture will not be filled in. Additionally, this welding process results in a flush surface over the contact sleeve, and avoids interference during implant.

Finally, at step 540, a tip 240 is formed on the distal end 215 of the lead I 0. The lead tip 240 is inserted into a heated mold where the tip 240 is formed from the mold. The tip 240 is then cooled and withdrawn from the mold. Alternatively, the tip 240 may be heat-butt-jointed to the lead 10.

Advantageously, this process of the present invention has many advantages over prior art techniques. For example, the present technique may be automated. Further, the present technique significantly reduces the manufacture time for leads and avoids the need for lengthy cure processes.

Those skilled in the art will recognize that the preferred embodiments may be altered or amended without departing from the true spirit and scope of the invention, as defined in the accompanying claims.

We claim:

1. An implantable lead having a distal end, a proximal end and a body, comprising in combination:
    (A) a flexible tubing member along an outside portion of the lead;
    (B) a coil member running along a central lumen portion of the lead, the coil having at least a first portion having a first pitch and at least a second portion having a second pitch;
    (C) at least two wire members forming the coil member, each wire member having a filar at a distal end that extends from the coil member, wherein the first pitch and second pitch are predetermined to allow the filars to be substantially collinear at a predetermined distance therebetween independent of wire member width and number; and
    (D) at least one contact sleeve positioned over an impression of the flexible tubing member and having an opening for receipt of the filar, the opening having a weld point coupling the filar to the contact sleeve.

2. A lead, as claimed in claim 1, wherein the flexible tubing is a polyurethane material.

3. A lead, as claimed in claim 1, wherein the first portion of the coil member is along the body of the lead and the second portion of the coil member is along the distal end of the lead.

4. A lead, as claimed in claim 1, further comprising:
    (E) a distal tip adjacent a distal end of the flexible tubing member.

5. A lead, as claimed in claim 1, further comprising:
    (E) a lumen extending through the coil for delivering a drug.

6. An implantable lead of claim 1, wherein the flexible tubing member has at least one impression.

7. An implantable lead having a distal end, a proximal end and a body, comprising in combination:
    (A) a coil member running along a central lumen portion of the lead, the coil having a first portion having a first pitch and a second portion having a second pitch;
    (B) at least two wire members forming the coil member, each wire member having a filar at a distal end that extends from the coil member, wherein the first pitch and second pitch are predetermined to allow the filars to be substantially collinear at a predetermined distance therebetween independent of wire member width and number;
    (C) a flexible tubing member formed over the coil member; and
    (D) at least one contact sleeve having a through radial hole for receipt of the filar, the filar being welded to the contact sleeve along the radial hole.

8. A lead, as claimed in claim 7, wherein the flexible tubing member is a polyurethane material.

9. A lead, as claimed in claim 7, wherein the flexible tubing member has at least one impression for receipt of the contact sleeve.

10. A lead, as claimed in claim 7, wherein the first portion of the coil member is along the body of the lead and the second portion of the coil member is along the distal end of the lead.

11. A lead, as claimed in claim 7, further comprising:
    (E) a distal tip that is heat formed at a distal end of the flexible tubing member.

12. A lead, as claimed in claim 7, further comprising:
    (E) a lumen extending through the coil for delivering a drug.

13. An implantable lead having a distal end, a proximal end and a body, comprising in combination:
    (A) a flexible tubing member along an outside portion of the lead;
    (B) a coil member running along a central lumen portion of the lead, the coil having at least a first portion having a first pitch and at least a second portion having a second pitch;
    (C) at least two wire members forming the coil member, each wire member having a filar at a distal end that extends from the coil member, wherein the filars are collinear at a predetermined distance therebetween being determined by the pitches of the coil member and being independent of wire member width and number; and (D) at least one contact sleeve positioned over an impression of the flexible tubing member and having an opening for receipt of the filar, the opening having a weld point coupling the filar to the contact sleeve.

14. A lead, as claimed in claim 13, wherein the flexible tubing member is made of a polyurethane material.

15. A lead, as claimed in claim 13, wherein the first portion of the coil member is along the body of the lead and the second portion of the coil member is along the distal end of the lead.

16. A lead, as claimed in claim 13, further comprising:
(E) a distal tip adjacent a distal end of the flexible tubing member.

17. A lead, as claimed in claim 13, further comprising:
(E) a lumen extending through the coil for delivering a drug.

18. A method of manufacturing an implantable lead comprising the steps of:
(A) forming a coil member comprising at least two wire members, the coil member having a fixed pitch portion and a variable pitch portion, each wire member having a filar member at a distal end, wherein the variable pitch portion is predetermined to allow the filars to be substantially collinear at a predetermined distance therebetween independent of wire member width and number;
(B) forming a flexible lead body over the coil member;
(C) extending the filar members of each of the wire members radially from the coil member at a predetermined portions along the variable pitch portion of the coil member;
(D) providing a contact sleeve over a portion of the lead body, the contact sleeve having a opening for receipt of the filar member; and
(E) welding the filar member to the contact sleeve.

19. A method, as claimed in claim 18, wherein the step of forming a flexible lead body further includes the step of forming impressions for placement of the contact sleeve.

20. A method, as claimed in claim 18, further comprising the step of:
(F) heat forming a tip at a distal end of the lead.

21. A method, as claimed in claim 19, wherein the step of forming impressions is performed by a technique selected from the group consisting of grinding and laser etching.

22. A method, as claimed in claim 21, further comprising the step of heat sealing the lead body to provide a final dimension for the impressions.

* * * * *